United States Patent
Liu

(10) Patent No.: US 10,860,741 B1
(45) Date of Patent: Dec. 8, 2020

(54) TELECOMMUNICATION PRIVACY PROTECTION USING A HIGH-LEVEL PROGRAMMING INTERFACE

(71) Applicant: 8x8, Inc., San Jose, CA (US)

(72) Inventor: Zhishen Liu, San Jose, CA (US)

(73) Assignee: 8x8, Inc., Campbell, CA (US)

( * ) Notice: Subject to any disclaimer, the term of this patent is extended or adjusted under 35 U.S.C. 154(b) by 230 days.

(21) Appl. No.: 16/013,655

(22) Filed: Jun. 20, 2018

Related U.S. Application Data

(60) Provisional application No. 62/524,027, filed on Jun. 23, 2017.

(51) Int. Cl.
*H04L 29/06* (2006.01)
*G06F 21/62* (2013.01)
*H04L 12/24* (2006.01)
*G16H 10/60* (2018.01)

(52) U.S. Cl.
CPC ......... *G06F 21/6245* (2013.01); *G16H 10/60* (2018.01); *H04L 41/0213* (2013.01); *H04L 67/42* (2013.01)

(58) Field of Classification Search
CPC . G06F 21/6245; H04L 41/0213; H04L 67/42; G16H 10/60
See application file for complete search history.

(56) References Cited

U.S. PATENT DOCUMENTS

| | | | |
|---|---|---|---|
| 7,403,604 B2 | 7/2008 | Mundra et al. |
| 8,064,909 B2 | 11/2011 | Spinelli et al. |
| 8,656,417 B2 | 2/2014 | May |
| 8,918,867 B1 | 12/2014 | Salour |
| 8,948,358 B1 | 2/2015 | Rengarajan et al. |
| 8,964,726 B2 | 2/2015 | Lawson et al. |
| 9,137,127 B2 | 9/2015 | Nowack et al. |
| 9,160,696 B2 | 10/2015 | Wilsher et al. |

(Continued)

FOREIGN PATENT DOCUMENTS

WO 0135579 5/2001

OTHER PUBLICATIONS

"Cisco Hosted Unified Communications Services", Cisco Product Data Sheet, Jun. 18, 2007 (retreived May 31, 2016) http://www.cisco.com/c/en/us/products/collateral/unified-communications/product_data_sheet0900aecd80670040.html.

*Primary Examiner* — Shawnchoy Rahman
(74) *Attorney, Agent, or Firm* — Crawford Maunu PLLC

(57) ABSTRACT

Certain aspects of the disclosure are directed to customized communication monitoring and alerts using a high-level programming interface. According to a specific example, a data communications server is configured and arranged to provide a database with virtual office features available to remotely-situated client entities. The data communications server is configured to provide to the client entities, a set of instructions written in a first programming language that defines a message exchange protocol, the set of instructions including aspects of the message exchange protocol to be populated with client-specific directives. The data communications server is further configured to receive from each client entity, client-specific sets of control data written in a second programming language that is compatible with the first programming language, and including privacy protection processes implemented for data communications including the one disparate client entity.

19 Claims, 6 Drawing Sheets

(56) References Cited

U.S. PATENT DOCUMENTS

| | | | |
|---|---|---|---|
| 9,240,966 B2 | 1/2016 | Wilsher et al. |
| 9,270,833 B2 | 2/2016 | Ballai et al. |
| 9,294,433 B1 | 3/2016 | Salour |
| 9,294,515 B2 | 3/2016 | Sayko |
| 9,306,982 B2 | 4/2016 | Lawson et al. |
| 9,338,064 B2 | 5/2016 | Stratton et al. |
| 9,344,573 B2 | 5/2016 | Wolthuis et al. |
| 9,407,597 B2 | 8/2016 | Lawson et al. |
| 9,426,116 B1 | 8/2016 | Salour |
| 9,455,949 B2 | 9/2016 | Lawson et al. |
| 9,456,008 B2 | 9/2016 | Lawson et al. |
| 9,459,925 B2 | 10/2016 | Lawson et al. |
| 9,459,926 B2 | 10/2016 | Shakirzyanov et al. |
| 2007/0047571 A1 | 3/2007 | Kandikonda et al. |
| 2007/0091800 A1 | 4/2007 | Corcoran |
| 2007/0115942 A1 | 5/2007 | Money et al. |
| 2008/0125077 A1 | 5/2008 | Velazquez et al. |
| 2009/0201916 A1 | 8/2009 | Caron et al. |
| 2010/0128709 A1 | 5/2010 | Liu et al. |
| 2010/0142516 A1 | 6/2010 | Lawson et al. |
| 2011/0170681 A1 | 7/2011 | Kole et al. |
| 2011/0320550 A1 | 12/2011 | Lawson et al. |
| 2012/0208495 A1 | 8/2012 | Lawson et al. |
| 2012/0303521 A1* | 8/2012 | Bous et al. |
| 2012/0304245 A1 | 11/2012 | Lawson et al. |
| 2013/0072153 A1 | 3/2013 | Lawson et al. |
| 2013/0212603 A1 | 8/2013 | Cooke et al. |
| 2013/0304929 A1 | 11/2013 | Fahlgren et al. |
| 2014/0044123 A1 | 2/2014 | Lawson et al. |
| 2014/0105372 A1 | 4/2014 | Nowack et al. |
| 2014/0270109 A1 | 9/2014 | Riahi et al. |
| 2018/0077160 A1* | 3/2018 | Call et al. |
| 2018/0091466 A1* | 3/2018 | Friedman et al. |

* cited by examiner

TELECOMMUNICATION PRIVACY PROTECTION USING A HIGH-LEVEL PROGRAMMING INTERFACE

OVERVIEW

Aspects of various embodiments are directed to communication and computing services. Data communications platforms have allowed individuals to transmit communications using broadband Internet connections in place of traditional telephone lines. A data communications endpoint device can use a broadband Internet connection to connect to a data communications server that is managed by a data communications service provider. The data communications server can handle communication routing and provide other data communications services for the data communications endpoint device.

Computing servers are increasingly being used to provide various data communications services over a network including, but not limited to, routing of Voice over Internet Protocol (VoIP) calls and/or data service providers for providing communications services such as messaging, video conferencing, management of data communications exchange servers, packet switching, traffic management, website hosting, remote data storage, remote computing services, and management of virtual computing environments, among other examples. For ease of reference, the various applications, systems and services that may be provided by such computing servers may be collectively referred to as data communications services.

The use of data communications services has been widespread and significant in terms of both numbers of users and types of services being made available. This growth may be attributable to any of a wide variety of socio-economic changes such as the mobility of users of these services, the types and reduced costs of portable communication tools, and the ever-evolving technology adapting to the personal and business needs of the communications users.

For business entities, the increased use of data communications services has been particularly complex, largely due to providing the same level of personal features to users from the vantage point of each business entity's communications platform. As examples, a data communications service provider can be providing such data communications services to a multitude of business entities each of which uses the provided services for a customized platform configured to provide communications services to a wide range of employees. For each such customized platform, it can be particularly burdensome for the data communications service provider to adjust and reconfigure the customized platform (of each respective business entity to which such services are being provided) each time a business entity (e.g., as requested by the entity's IT department, employee(s) or others) changes in terms of the employee's communications equipment/endpoint devices.

SUMMARY

Various example embodiments are directed to issues such as those addressed above and/or others which may become apparent from the following disclosure concerning systems and methods for communication privacy protection using a high-level programming interface.

Embodiments are directed toward methods for use in communications systems employing a data communications server operated by a communications provider, where the data communications server is on the data communications provider side use to provide data communications services to a multitude of client entities. In such contexts, the data communications server may be referred to as a data communications provider server. In such systems, the data communications server includes one or more computer processor circuits (configured with access to databases stored in memory circuits) and configured to act as a communications-control engine for routing, processing communications and/or providing related communications services on behalf of client entities. Such client entities may be exemplified respectively as the above-noted businesses with employees ranging in number from just a few to thousands, and being located/mobile for communications services in any of a multitude of venues. In these embodiments, such methods use the communication-control engine to provide such communications services by receiving data communications from data communications endpoint devices, and identifying client-specific sets of control data (e.g., providing directives or commands with communication processing data), derived from programming instructions written in a first instruction-configurable/programmable language that is associated with a message exchange protocol that is used between the data communications routing server and data sources. Examples of such client-specific sets of control data may include other forms of code providing data and/or instructions over an interface facilitating communication between the communications provider and the data communications endpoint devices. Such methods execute the client-specific sets of control data to make decisions on how to route communications placed by the data communications endpoint devices, and to identify a set of instructions (written in a second instruction-configurable/programmable language) associated with the routing decisions.

The first and second programmable languages may be similar, in that both languages are derivatives of a same type of programmable language, but the first and second programmable languages may differ in terms of content and use. The first programmable language may identify communication processing directives provided to the communications provider by the client entity, whereas the second programmable language may identify communication routing directives as provided by the communications provider. Such methods execute the set of instructions to retrieve data from the data sources maintained by the communications provider, and provide, in response to the data, communication control functionality for the data communications placed by the endpoint device. The first and second programming languages are related languages, whether indirectly or directly related via at least one level of translation. For example, or analogous to, C++, compiled to assembly/object level code and a converted to higher-level, different language or set of instructions.

Certain embodiments are directed toward an apparatus for privacy protection in a communication system. The apparatus may comprise a communication server configured to interface with remotely-situated client entities using a first programming language that relates to a message exchange protocol between a data communications provider and data sources. The communication server is configured and arranged to provide data communications for a plurality of endpoint devices, each respectively associated with an account of a respective one of the plurality of disparate client entities, by routing the data communications for the endpoint of each of the client entities. The apparatus further includes a database storing client-specific private data, and a processing circuit communicatively coupled to the database and the communication server. In accordance with examples of the present disclosure, the processing circuit is configured and arranged to privately adjust routing or processing of the data communications for one of the disparate client entities. The processing circuit is configured to adjust routing or processing of the data communications by generating for the client entity, client-specific control data based on programming instructions received from the client entity over the message exchange protocol. As described herein, the programming instructions correspond to a second programming language that is compatible with the first programming language and includes privacy protection processes implemented for data communications including the one disparate client entity. In response to receipt of data communications involving the client entity, the processing circuit is configured and arranged to communicate the client-specific private data based on the client-specific control data.

Certain embodiments are directed toward an apparatus for privacy protection in a communication system. In such embodiments, the apparatus comprises a database storing a set of client-specific private data, a computing server, and a processing circuit. The computing server is configured and arranged to provide data communications for a plurality of extensions, each respectively associated with an account of a respective client entity, and interface with a data communications server configured and arranged to provide virtual office features to the extensions based on a subscription. The processing circuit is communicatively coupled to the computing server and the database, and is configured and arranged to receive from the data communications server, a set of instructions written in a first programming language that relates to a message exchange protocol between the data communications server and data sources. The processing circuit is further configured and arranged to generate programming instructions corresponding to a second programming language that is compatible with the first programming language and including privacy protection processes implemented for data communications including the respective client entity. Moreover, the processing circuit is configured and arranged to facilitate private routing or processing of the client-specific private data by the data communications server by communicating the programming instructions including the privacy protection processes to the data communications server.

The above discussion/summary is not intended to describe each embodiment or every implementation of the present disclosure. The figures and detailed description that follow also exemplify various embodiments.

BRIEF DESCRIPTION OF FIGURES

Various example embodiments may be more completely understood in consideration of the following detailed description in connection with the accompanying drawings, in which.

Figure 1:
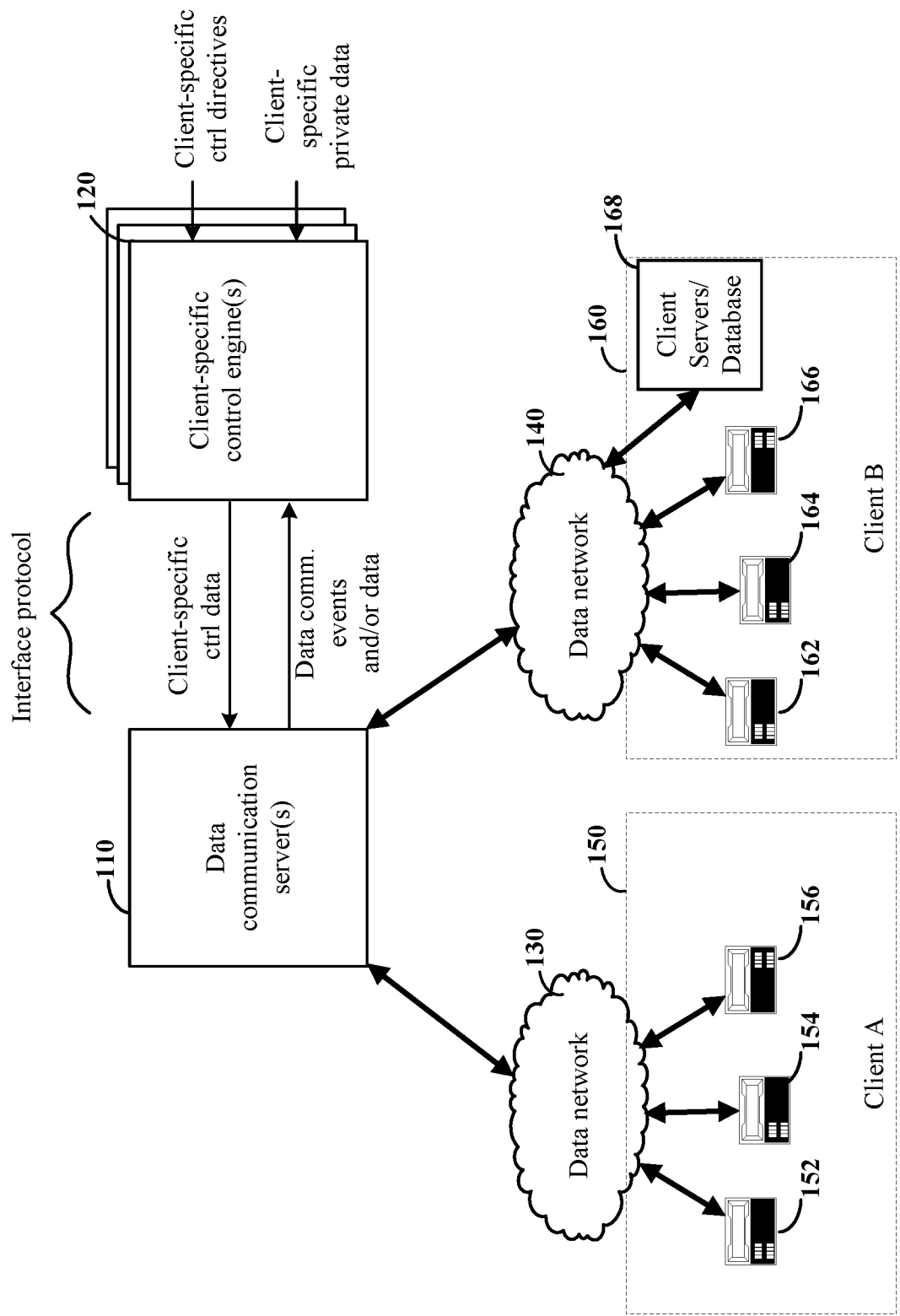
FIG. 1 is a diagram for communication privacy protection using a high-level programming interface, consistent with embodiments of the present disclosure.

While various embodiments discussed herein are amenable to modifications and alternative forms, aspects thereof have been shown by way of example in the drawings and will be described in detail. It should be understood, however, that the intention is not to limit the disclosure to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Aspects of the present disclosure are believed to be applicable to a variety of different types of apparatuses, systems and methods involving communications privacy protection using a high-level programming interface. In certain implementations, aspects of the present disclosure have been shown to be beneficial when used in the context of providing data communications services. While the present disclosure is not necessarily limited to such data communications systems as described herein, for purposes of facilitating understanding and appreciation of certain embodiments, the following discussion uses such data communications-based services and systems in the context and on behalf of communications platforms of client entities which subscribe to such services from a data communications service provider (with a server).

In the following description, various specific details are set forth to describe specific examples presented herein. It should be apparent to one skilled in the art, however, that one or more other examples and/or variations of these examples may be practiced without all the specific details given below. In other instances, well known features have not been described in detail so as not to obscure the description of the examples herein. For ease of illustration, the different diagrams can refer to the same elements, more specific embodiments, or additional instances of the same element. Also, although aspects and features may in some cases be described in individual figures, it will be appreciated that features from one figure or embodiment can be combined with features of another figure or embodiment even when the combination is not explicitly shown or explicitly described as a combination. For ease of explanation, some examples may be primarily described with reference to data communication servers configured to provide data communication services for endpoints of a plurality of different client accounts. It is understood that the various examples may be adapted for use with computer servers configured to provide various other remote services, including, but not limited to: website hosting, remote data storage, remote computing services, virtual computing environments, enterprise communications, virtual contact center, and other services.

Some remote service providers customize their services for different customers. This might include customizable auto attendants, communication routing, communication forwarding, voicemail, or other features. For particularly large clients with many different telephone accounts and numbers, implementing and updating these types of customizations can be a significant undertaking. Moreover, some clients may maintain private data, such as patient records, financial records, and/or social security information, among others, such that the private data must be protected while such services are provided. Certain embodiments of the present disclosure are directed toward an interface that allows a client-specific control engine to access and dynamically adjust the manner in which remote services are provided for the users of a client account during operation, while maintaining the integrity and security of the underlying system for providing the remote services, and while protecting the private data in accordance with various laws, policies, and/or best practices.

According to certain embodiments, a data communication system may be configured to allow a client-specific control engine to dynamically modify and control the communication flow and processing at different levels within the system, including (re)routing of incoming communications generally and by way of private branch exchanges (PBXs) and Internet Protocol PBXs (or IP PBXs) to provide intelligent routing relative to receptionists and direct dial numbers for individuals using the IP PBXs. Within these constraints, a customer can write code that self-describes the building blocks or particular configurations used in the customer's particular application, which can be interpreted and executed by the data communications provider. In various embodiments, the building blocks or particular configurations and the data communications servers that execute the building blocks or particular configurations can be configured to interface with other sources of data and control. This can include, for example, flow control decisions that are based upon code running on the client side or on the provider side. As non-limiting examples, a client-side computer system could run code that is written using JavaScript or TCL while a server-side computer system might run code that is written using PHP: Hypertext Preprocessor (PHP), NodeJS, Python, Scala, Ruby, .Net, or other web languages.

Rules of various complexity can be used for routing incoming communications, whether to one or more receptionists, directly to extensions, to voicemail, or for other communication routing purposes. The logic used for the routing decisions can be based upon directives and related data shared across multiple PBXs, data that can be dynamically changed, and upon rules and logic that can be defined according to multiple tiers of communication routing decisions. For example, a large company may have many different offices or store locations. Portions of the communication routing and processing can be shared across the entire company. Other portions could be shared with subsets or groups (e.g., groups based upon geographic regions or countries or based upon different company divisions). Still further portions can be set based upon individuals being called. Such aspects can facilitate the configuration, management, and updating the data communication system, particularly in situations where there are many thousands of extension rules can be a difficult proposition.

According to certain embodiments, the data communication system provides inbound and outbound communication routing for one or more PBXs. A PBX is a telephone system that switches calls between enterprise users on local lines while allowing all users to share a certain number of external phone lines. External phone lines are telephone lines that are supported by telephone carriers as being individually addressable within the public switched telephone network (PSTN). For example, a PBX can use extensions to direct calls to many phones after a caller first makes a call to a shared number. As another example, a PBX can provide direct Inward Dialing (DID). DID is a service where a telephone carrier provides a block of telephone numbers that are each routed to a PBX system rather than to individual telephone lines. Using DID, individual phone numbers can be provided to each person or workstation without separate physical lines into the PBX for each possible connection.

According to certain example embodiments, a data communications system is configured as a Platform as a Service (PaaS) that provides a user with access to, among other things, telephone communication routing control, PBX functions, computer telephony integration (CTI), and data analytics (in this context the user can refer to, e.g., person, group, server or CPU, or subscribing business entity). Embodiments of the present disclosure are directed toward an interface that allows users of the data communications system solution to access data communications telephone capabilities of the underlying system, including its hardware and software components, while maintaining the integrity and security of the underlying system. Particular embodiments are directed toward a communications solution that allows for protection of client-specific private data while also customizing various virtual office features for end-users of the data communications system. The virtual office features may be adjusted for such end users, while also providing the ability to interface with data sources that are either part of the underlying system or external to the communications solution, and may include at least in part private data. These features can be used in combination with a communication routing system that can be configured and adjusted in a scalable manner. As end-users can customize the various virtual office features provided, so too can the client entity and/or end-users specify data that is considered private (e.g., sensitive), and a manner in which such private data is to be protected.

For instance, consistent with examples of the present disclosure, a client entity may specify particular processing and/or analytics to be implemented based on the identification of private data, such that routing and/or control decisions may be made without exposing the private data. Such a client entity may include a startup company that uses the virtual office features provided by the data communications provider to provide a new video chat service for its customers. The client entity may instruct the data communications provider (via the high-level programming language) to make routing and/or processing decisions based on the private data of its customers without exposing the private data to the data communications provider.

As an additional or alternative example, a client entity such as a hospital may use the virtual office features provided by the data communications provider to facilitate online doctor consultations. In such examples, analytics performed by the client entity may determine the sensitivity of data to be communicated, and can adjust routing/processing/control of the virtual office features based on the sensitivity of the data to be communicated (e.g., patient data) without violating patient privacy laws such as the Health Insurance Portability and Accountability Act (HIPAA). To illustrate, a remotely located patient may place a communication to an online consultation service. Communication events and/or user input are forwarded from a data communications provider side communication routing engine to client-side communication routing engine that has access to private patient data. The client-side communication routing engine may perform one or more client specific actions using the private data and without exposing the private data to the data communications provider. In another illustration, a remotely located patient may place a communication to an online consultation service. A data communications provider-side communication routing engine may select a medical practitioner for the patient consult based on private patient records (e.g., a doctor that consulted/examined patient last), and the client-side communication routing engine may forward the patient's medical records to the selected medical practitioner. The client-side communication routing engine may further prompt the provider-side communication routing engine to route communications from the patient to selected/identified medical practitioner. In yet another illustration applicable to the medical practice, the data communications system may be used to customize routing of incoming communications to patients admitted in a medical facility, using private patient data (e.g., communications to the patient are routed to voicemail if the patient is in a procedure and otherwise communications to the patient are routed to the patient's room in the medical facility).

As an additional or alternative example, a client entity having a multitude of franchises may utilize the data communications system to ensure that private data of one franchise location is separate and protected from private data of another franchise location.

The ability to access the underlying data communications services, including communication routing and communication control engines, can provide a platform that is both flexible and simple to implement from the viewpoints of both the data communications provider and the customers of the data communications provider. The communications solution can be configured to modify the virtual office features available to different end-users, and to control the communication flow and processing at all levels within the system, including (re)routing of incoming communications to different PBXs. When compared to an add-on type service where a communication is first handled by a separate PBX, the communications solution may offer a number of advantages and additional features including, but not limited to, increased communication routing capabilities, scalability, and reduced complexity. For instance, access to PBX functions allows for simple communication redirection to extensions or DID numbers provided by the PBX. Moreover, the communications solution coordinates and routes communications between multiple PBXs using an initial communication routing switch. Communications initially routed to a particular PBX can still be rerouted to a different PBX using the initial communication routing switch. Yet further, the communications solution allows a data communications client having multiple end-users to customize the various virtual office features provided to the end-users, without compromising the security of the underlying system or requiring additional customization by the data communications provider.

The data communications servers providing the underlying function for the data communications system can be configured to utilize a programmable (or configurable) communication protocol such as a high-level, domain-specific programming language as might be implemented with respective data communications servers providing data communications routing and IP PBX functions on respective sides of an interface configured to facilitate the communications via the defined protocol. A particular example of a data communications server may use session initiation protocol (SIP) to handle various communication functions (e.g., call setup and tear down). However, the various embodiments discussed herein are not necessarily limited thereto. Consistent with the above and in other embodiments disclosed herein, the data communications servers can be configured to establish a portion of the communication from the data communications endpoint devices to another data communications endpoint device or to endpoints on the PSTN through use of a PSTN gateway. Each of the endpoint devices includes data communications-enabled circuitry, and may include for example, IP phones, smart phones, tablets, desktop computers, plain old telephone service (POTS) telephones, and cellular-capable devices among other example devices with circuitry configured and arranged to facilitate sending and receipt of data communications.

According to more specific example embodiments, a high-level domain-specific programmable communication protocol (e.g., specific to customer-entity domains) uses one or more languages which are defined using a markup language as the basis for the language structure. Particular implementations relate to the use of at least two domain-specific languages, one that can be used for initial communication routing and the other for providing more complex and specific communication processing functions. More particular example embodiments use an eXtensible Markup Language (XML). An XML model defines the constraints on the high-level language, including defining the set of valid commands that can be carried out by the data communications servers. Within these constraints, a customer can write XML code that self-describes the building blocks or particular configurations used in the customer's particular application. For instance, a common set of instructions, written in the high-level language (e.g., an XML language) may be provided by a data communications provider to client entities. The common set of instructions may form a template to be populated with client-specific directives, the populated template forming programming instructions that instruct the data communications provider how a particular client entity is to be configured for various data communications services. The data communications provider may derive client-specific sets of control data from the programming instructions, and store the client-specific sets of control data for subsequent retrieval and implementation. In such a manner, the data communications provider may provide a lightweight and simplified set of instructions to client entities, and client entities may provide the data communications provider with instructions to customize the virtual office services for that particular client entity. XML also allows for various different data structures to be embedded into the XML, document or file. For example, a script written in JavaScript can be embedded as character data that the data communications servers are configured to identify and execute. Unless otherwise stated, the use of XML in connection with various embodiments does not necessarily limit the corresponding embodiments, such as limiting the embodiments to the use of only an XML-based language(s). As used herein, such domain-specific programming language(s) are referred to as high-level markup languages (e.g., XML derivative languages or XML-type languages).

Various examples of such XML derivative languages are exemplified in the Appendix as attached to the underlying U.S. Provisional Patent document (Application No. 62/524,027 filed Jun. 23, 2017) incorporated herein by reference. In certain example data communications applications, two XML-type languages are implemented as a communication processing XML and a communication routing XML, respectively as XML derivative languages corresponding to XML but customized for processing data communications on the side of the interface operating on behalf of customer entities and on the other side of the interface for higher level processing (including, for example, communication routing) by the data communications service provider. Such XML derivative languages can be written specific to types of functionality as needed for various customer entities, thereby allowing developers to program communication processing logic or service execution logic with both XML building blocks and JavaScript/TCL, or other scripting languages best suited to levels (e.g., in terms of quantity range) of a customer's endpoint devices and/or in terms of complexity of the data communications-based media functionality and evolving demands expected by a customer. In certain implementations, XML derivative languages allow data communications customer developers to program and integrate data communications flow (e.g., as provided by a cloud-based data communications service) with customer or third party application servers and databases. In particular, the communication flow can include a connection that is used as part of communication routing decisions and communication processing options that are related to one or more receptionists that can answer communications to a group of endpoint devices. The system allows different levels of communication control logic to be implemented in a manner that can facilitate scalability of the system of large organizations with many endpoint devices and/or end-users and with complex organizational structures that have corresponding complex communication routing requirements.

For ease of discussion, various embodiments are discussed in terms of XML, and more particularly, XML derivative languages. The skilled artisan would appreciate that each such XML-type embodiment is not necessarily limited to XML, XML derivative languages, or variants of XML. The corresponding directives, control and related communications data can be provided in documents corresponding to other languages and/or communications protocols; for example, one such programming language can be used for initial communication routing and another programming language can be used for providing more complex and specific communication processing functions.

According to particular embodiments, an XML engine can respond to a communication, or other event, by sending requests to a web server and get XML derivative documents (e.g. a set of instructions) for processing (providing a set of directives or instructions for taking action), thereby operating in a stateless manner that is similar to how an Internet browser, or similar interface uses Hypertext Markup Language (HTML). The XML engine can interpret a received XML derivative document to identify XML building blocks that are then rendered (i.e., executed). Each building block can define logic relating to one or more functions, such as for voice, communication control, and flow control logic. The XML engine may also execute other types of code, such as JavaScript, to create dynamic content (e.g., dynamically generated XML-derivative) for client-side flow control. Each XML derivative document may have uniform resource identifier (URI) links to a web server for iterative processing, or it may include query requests for retrieving data from various sources of data. A query could be formatted for consistency with the source of the data (e.g., by using JavaScript Object Notation (JSON) to retrieve data from third party application servers or from the data communications server provider's cloud database). This information can then be used to drive communication flow or communication control functionality and decisions.

As applicable to routing decisions relating to receptionists, an incoming communication can be processed according to an XML document with instructions (e.g., client-specific sets of control data) for determining whether communications route to a receptionist, directly to a called endpoint device, or are routed and processed in some other manner. Moreover, the instructions may specify a manner in which such calls/communications are routed and/or handled so as to protect the privacy of the underlying data. As an example, the XML document could include a set of global rules for determining how to handle communications to endpoints of a customer (e.g., a large business with many individuals and corresponding endpoint devices). XML documents can also specify local rules for routing communications (e.g., to endpoint devices, voicemail, auto communication attendants), or otherwise processing the communication. The local rules might be used if global rules specify that the communication is not routed to a receptionist, or if the receptionist rejects or forwards the communication on. Each of the local and global rules can be driven, at least in part, by data retrieved from a data source, such as a client server or database. Similarly, such rules can be driven, at least in part, by a determined level of sensitivity of the retrieved data. As an example, the global rules could access a customer database that includes lists of caller IDs that are handled differently. The communication routing data communications server does not need to have direct access to the lists of caller IDs (which might be confidential lists and thereby represent a security risk if shared directly with the data communications server). Rather, the data communications server can send a query that includes a specific caller ID number of an incoming communication. In response to the query, information can be provided that indicates how to process the communication (e.g., whether to route the incoming communication to a receptionist or directly to the dialed endpoint device).

According to various embodiments, the high-level programming language allows a programmer access to the communications solution by way of a controlled and limited set of communication control functionality in the form of communication processing and routing operations. The limitations on the operations can be particularly useful for allowing programming control to be placed into the hands of different customers of the provider of the data communications servers. For example, the provider can update or make other changes to how the data communications servers are configured without requiring modification to documents written to use the high-level language, which might otherwise be required to account for the changes. Moreover, the data communications servers and their data can be protected from poor programming decisions (intentional or otherwise) by tightly controlling the extent that the documents provide control of, or access to, the inner workings of the data communications servers. In a similar manner, in various embodiments, the data communications customer can update or make changes to the various virtual office features that are provided to end-users to provide a customizable solution for each data communications customer and their respective end-users.

In various embodiments, the high-level programming language and the data communications servers that execute the high-level programming language can be configured to interface with other sources of data and control. This can include, for example, flow control decisions that are based upon code running on the client side or on the server side. As non-limiting examples, a client-side computer system could run code that is written using JavaScript or TCL while a server-side computer system might run code that is written using PHP: Hypertext Preprocessor (PHP), NodeJS, Python, Scala, Ruby, .Net, or other web languages.

In example embodiments, a data communications provider server may be configured to provide customized virtual office features (e.g., data communications services) to clients of the data communications provider. The data communications provider server may include one or more computer processor circuits coupled to memory circuits and configured to interface with a plurality of remotely-situated client entities. The data communications provider server can be configured and arranged to provide a database with a set of virtual office features including client-specific communication routing functions. The set of virtual office features, including communication routing functions, may be available to remotely-situated client entities based on a subscription provided by the data communications provider. The data communications server can provide to the client entities, a set of instructions written in a first programming language that is associated with a message exchange protocol between the data communications provider server and data sources.

The set of instructions can include aspects and/or portions that are to be populated (e.g., supplemented) with client-specific directives associated with virtual office features available to client entities. For example, the data communications provider server can provide to each client entity, a common set of instructions defining various aspects of virtual office features provided to the client entities. This set of instructions may serve as a sort of template, or default configuration, of virtual office features provided to the client entities. In turn, the client entities may provide to the data communications provider server, programming instructions from which client-specific sets of control data are derived, which allow the data communications provider server to customize the virtual office features provided to each particular client entity. The programming instructions can be written in a second programming language that is compatible with the first programming language (e.g., the language in which the set of instructions from the data communications provider are written in). Moreover, the programming instructions can be generated by the client entity (by a client-specific control engine) by populating or combining the set of instructions received from the data communications provider server with a set of directives associated with the virtual office features available to the client entity. The client-specific sets of control data, derived from the programming instructions and stored for subsequent retrieval and implementation by the data communications provider, can be used to provide an adjusted set of features to end-users of the client entities (e.g., based on and according to the client-specific sets of control data). Similarly, such programming instructions can specify protection processes implemented for an entire client entity and/or for specified subgroups of the client entity in order to protect the privacy of the underlying data communicated via the data communications system.

The adjusted set of virtual office features may be a subset of the virtual office features to which the client entity has subscribed. For example, a client entity such as a fitness company may subscribe to a particular set of communications services hosted by the data communications server. The client entity may have a number of franchises located in different geographic regions, and each franchise location may have different needs for communications services. As such, the client entity may wish to provide different types and/or different configurations of data communications services for its different franchise locations. In such a manner, the data communications server may provide an adjusted set of features to end-users of the client entities according to client-specific sets of control data. In another non-limiting example, the client entity may utilize a number of PBXs or IPBXs, and may segment the various end-users among the different PBXs, such that incoming communications are routed to one of the many PBXs associated with the client entity.

The client-specific sets of control data, associate with each respective client entity, may define aspects of the set of adjusted virtual office features provided to that particular client entity. As described herein, the programming instructions received by the data communications provider server from the client server may be written in a programming language that is associated with a message exchange protocol between the data communications provider server and data sources. For instance, the programming instructions, written in the programming language, may specify communication handling procedures to be implemented for end-users of the client entity, or a manner in which the data communications services may integrate with other network applications used by the client entity (e.g., client-specific network applications), among other examples. Data from the client-specific network applications may be imported to the virtual office features using privacy processes specified by the client entity. For instance, contacts from a client-specific email application may be imported to the virtual office features, allowing those same contacts to be accessed using the data communications system, while at the same time preventing the dissemination of the contacts to other client entities of the data communications system. In another non-limiting example, end-users may schedule conference communications using the data communications system and by importing data from a client-specific calendar and/or scheduling application while preventing the client-specific calendar from being shared with other client entities of the data communications system.

The programming instructions provided by the client entity may define various aspects of the virtual office features provided to end-users of the client entity. For instance, the programming instructions may define handling procedures of phone communications and/or conference communications for end-users of the client entity. The programming instructions may define a manner in which phone communications to and/or from the end-users are routed upon receipt. Similarly, the programming instructions may define a communication queue process for communications placed to the end-users, and/or designate an automated communication attendant to route data communications placed to the end-users. For example, a data communications client may instruct a data communications provider to configure the client to queue incoming communications, to assign incoming communications to one or a plurality of communication queues purchased according to a subscription, and to limit a number of communications to be placed in each of the communication queues. The data communications client may also instruct the data communications provider server to configure the client entity to create subgroups of end-users, such that incoming communications may be routed to a particular subgroup of end-users. Data encryption techniques may be specified for particular types of data, such that the data is not communicated to end-users via the data communications system without compliance with the encryption processes. Similarly, distribution of private data may be limited such that it may only be sent to specified people and/or groups of people. For instance, the programming instructions may specify that patient data may only be communicated to a medical practitioner and not to other patients. In another illustration, the programming instructions may specify that business data may only be communicated to end-points in a particular geographic region and/or to particular individuals.

The programming may also define system integration processes. Each client entity may utilize a number of network applications to support daily operations. For instance, the client entity may utilize an email application, an appointment scheduling application, and/or a messaging application, among other examples. The adjusted virtual office features provided to the end-users by the data communications server may be configured to define a manner in which the adjusted virtual office features operate in collaboration with the different network applications of the client entity. For example, the virtual office features provided by the data communications server may collaborate with the client's electronic medical records system, allowing end users to communicate electronic medical records to other end users, using the virtual office features.

Further, programming instructions received from the client entity may customize the virtual office features provided to end-users by defining a manner in which the set of adjusted virtual office features are accessed by mobile devices of the end-users. For instance, some types of client data may be prevented from communication over mobile devices and/or additional privacy protection processes may be implemented if the client data is communicated over a mobile device.

In various embodiments, a data communications client server may be provided, comprising one or more computer processor circuits coupled to memory circuits and configured to interface with the data communications provider server. As described herein, the data communications provider server can be configured to provide a database of virtual office features available based on a subscription. Similarly, the data communications client server can receive from the data communications provider server, a set of instructions written in a first programming language that defines a message exchange protocol between the data communications provider server and data sources. The data communications client server can further generate client-specific sets of control data written in a second programming language that is a subset of the first programming language. The second programming language may be considered a subset of the first programming language, and is associated with virtual office features available to the client entity. For instance, the client-specific sets of control data, provided in the second programming language, may further define and/or adjust the virtual office features provided to a client entity and/or end-users of the client entity.

The data communications client server can transmit to the data communications provider server, programming instructions written in the programming language such that the adjusted virtual office features may be configured. The data communications client server can access the set of adjusted virtual office features provided by the data communications provider server. In some instances, the client entity can allow the data communications provider to indirectly access data sources of the client entity. For example, the client entity can specify a URI that points to the data communications client server and specifies an associated query. The data communications client server can execute, for example, a local script that may rely upon customer data. The script can generate a response in the particular programming language, and the data communications provider server can then carry out communication routing, or other communication control functions, based upon the response and without ever having direct access to the customer data. As such, the data communications client server can be configured to provide programming instructions from which client-specific control data are derived, where the client-specific control data instructs the data communications provider server to retrieve data from the data sources based on the accessed set of adjusted virtual office features. The data communications client server may provide, in response to the retrieved data, communication control functionality to end-users of the client entity based on the accessed set of adjusted virtual office features.

Consistent with various embodiments of the present disclosure, programming instructions provided by the data communications client server to the data communications provider server may define various aspects of the virtual office features provided to client entities and/or end-users of client entities. For instance, a client entity may wish to provide different virtual office features to different subgroups of end-users, and/or to configure different virtual office features differently for different subgroups of end-users. For instance, the client entity may wish to protect different types of data for different groups and/or subgroups of end-users, and/or to configure different privacy protection processes for different groups and/or subgroups of end-users. Such subgroups may differentiate business units of end-users that have different needs for virtual office features compared to other business units. As such, client-specific sets of control data may define a plurality of end-user subgroups of the client entity, and the data communications client server may be configured to provide access to the set of adjusted virtual office features according to permissions of the end-user subgroups. Similarly, the programming instructions may define a plurality of data subscriptions to be included in the set of adjusted virtual office features, and the data communications client server may be configured to access the plurality of data subscriptions using the data communications provider server.

Programming instructions may be generated by a client server responsive and according to client-specific directives. Consistent with the above-characterized embodiments, at the client side of the data communications services, the client's computer-based processing resource (e.g., by the client-specific control engine) generates and submits programming instructions for assessment and use by the data communications service provider. Client-specific control data may be derived from the programming instructions and stored for subsequent retrieval and implementation by the data communications service provider. In a typical implementation, these programming instructions can be realized using codes or one or more commands (or a script of program-created commands). As examples, such codes or command sets can be implemented using a variety of programming control approaches. These approaches include, for example, a programming language (such as C++, XML, JAVA, HTML, SQL, etc.) common to both the client-specific control engine and to the data communications service provider, which receives the client-specific sets of control data (submitted from the client side) for adjusting the data communications services being provided to the submitting client.

By using a common interface protocol (e.g., the programming language, codes or command sets) which is understood by the data communications service provider, authentication and updating for added (telephony) services is readily achieved automatically and remotely without burdening the data communications service provider with cost-intensive set up procedures. Depending on the level of services being added/changed for each client, and/or depending on the client's manual-operator and/or automated technology, the programming instructions can be generated and submitted in various (coded) ways such as described above and also, for example, by dial tone input generated remotely on behalf of each client, by smartphone app specific to the client, by voice recognition, or combinations thereof. The client-specific sets of control data for a particular client entity may be generated based on various data metrics including, for example, data communication events or data received from the data communication server, client-specific directives received in the form of user input (e.g., input via dial-tones and/or GUI), data acquired from a client (e.g., from a client database), and/or data provided by third parties (e.g., third party monitoring services).

To provide a simplified, yet customizable solution that protects the security of the underlying data communications system and client entity data, the set of adjusted virtual office features may be provided to the end-users of the particular client entity in a programming language that includes communication flow commands for communication routing logic (such as an XML language, XML-derivative language, or other language described herein). Moreover, the virtual office features may be dynamically adjusted to account for changing needs of the client entity. For instance, data associated with the client entity (or end-users of the client entity) may at one point in time be considered private (or "sensitive") data, and at another point in time be considered public data (or no longer private/sensitive). As such, the set of adjusted virtual office features and the privacy settings associated therewith may be revised via the data communications server, responsive and according to additional sets of client-specific control data received from the particular client entity. As the client entity grows (or constricts, as the case may be), the client entity may adjust policies that govern such privacy policies. Similarly, as additional data protection processes are developed, so too can the programming instructions be revised to include additional and/or different data protection processes to ensure the privacy of the underlying data.

Turning now to the figures, FIG. 1 is a diagram for communication privacy protection using a high-level programming interface, consistent with embodiments of the present disclosure. The system includes a computing server 110 configured to provide data communications for a plurality of endpoint devices 152, 154, 156, 162, 164, and 166 connected in one or more data networks 130 and 140. The endpoint devices may include data communications-enabled devices (e.g., IP phones, smart phones, tablets, and/or desktop computers with appropriate data communications software applications) and/or non-data communications endpoint devices (e.g., plain old telephone service (POTS) telephones and cellular-capable devices). Each endpoint device is respectively associated with an account of a respective client. Endpoint devices may be associated with a particular client account by registering the endpoint device with a particular client account serviced by the data communication server. Registered devices for each client account may be listed in a respective account settings file (not shown) stored by the data communication servers 110. In this example, endpoint devices 152, 154, and 156 are associated within an account 150 for a first client A and endpoint devices 162, 164, and 166 are associated within an account 160 for a second client B.

The system includes one or more processing circuits configured to implement client-specific control engines 120, which are configured to adjust the data communications provided for each client account according to a respective set of control directives. For instance, the client-specific control engines 120 may adjust routing of a data communication for a client by providing programming instructions (from which client-specific sets of control data are derived) to the data communication server 110. For example, the client-specific control engines 120 may generate client-specific sets of control data by processing the respective set of control directives for the account in response to data communication event data or other data prompts received from the data communication server(s) 110. For instance, the control directives for a client account may be configured to adjust routing of a particular data communication in response to communication event data indicating a new incoming communication to an endpoint of the client account.

The control directives for a client account may generate the programming instructions based on various data metrics including, for example, data communication events or data received from the data communication server, user input (e.g., input via dial-tones and/or GUI), data acquired from a client (e.g., from a client database), and/or data provided by third parties (e.g., third party monitoring services). The client-specific control engines 120 communicate the client-specific control data to the data communication server(s) using an interface protocol having an instruction format that is independent of an instruction format used to implement the client-specific control engines 120 and/or client-specific control directives. The independent instruction format of the interface protocol allows clients to write programming instructions including complex logic and various data sources, for example, using various different high-level languages without regard to the particular language used to implement or communicate with the data communications provider server. In some embodiments, the instruction set of the interface protocol may be configured to limit customer control over certain data communication settings—thereby preventing clients from disrupting operations of the computing service with faulty client-specified directive code.

Different embodiments may implement the client-specific control engines 120 in various locations. For example, client-specific control engines 120 for one or more client accounts may be implemented in a central server connected to, or incorporated with, the data communication server(s) 110. Additionally or alternatively, one or more client-specific control engine(s) 120 may be implemented by one or more processing circuits maintained by the client (e.g., server/database 168). Similarly, the control directives may be stored locally within the client-specific control engines, or stored remotely (e.g., in a centralized database, in a database maintained by the client or a combination thereof).

As previously described, client-specific control engines may be used to facilitate adjustment of a variety of virtual office features including, for example, data communication services such as data communications, audio and/or video conferencing, IPBX exchange servers, packet switching, and traffic management as well as non-data communications services including, but not limited to, website hosting, remote data storage, remote computing services, virtual computing environments. One or more of such virtual office features may be provided, for example, by a cloud computing network having one or more servers configurable to provide a data communications system for a plurality of clients. Moreover, the client-specific control engines 120 may access client-specific private data and communicate the client-specific private data in accordance with privacy processes specified by the client entity. In such a manner, the private data may be communicated over the data communications system without exposing the private data to the data communications system and/or to other client entities of the data communications system.

Figure 2:
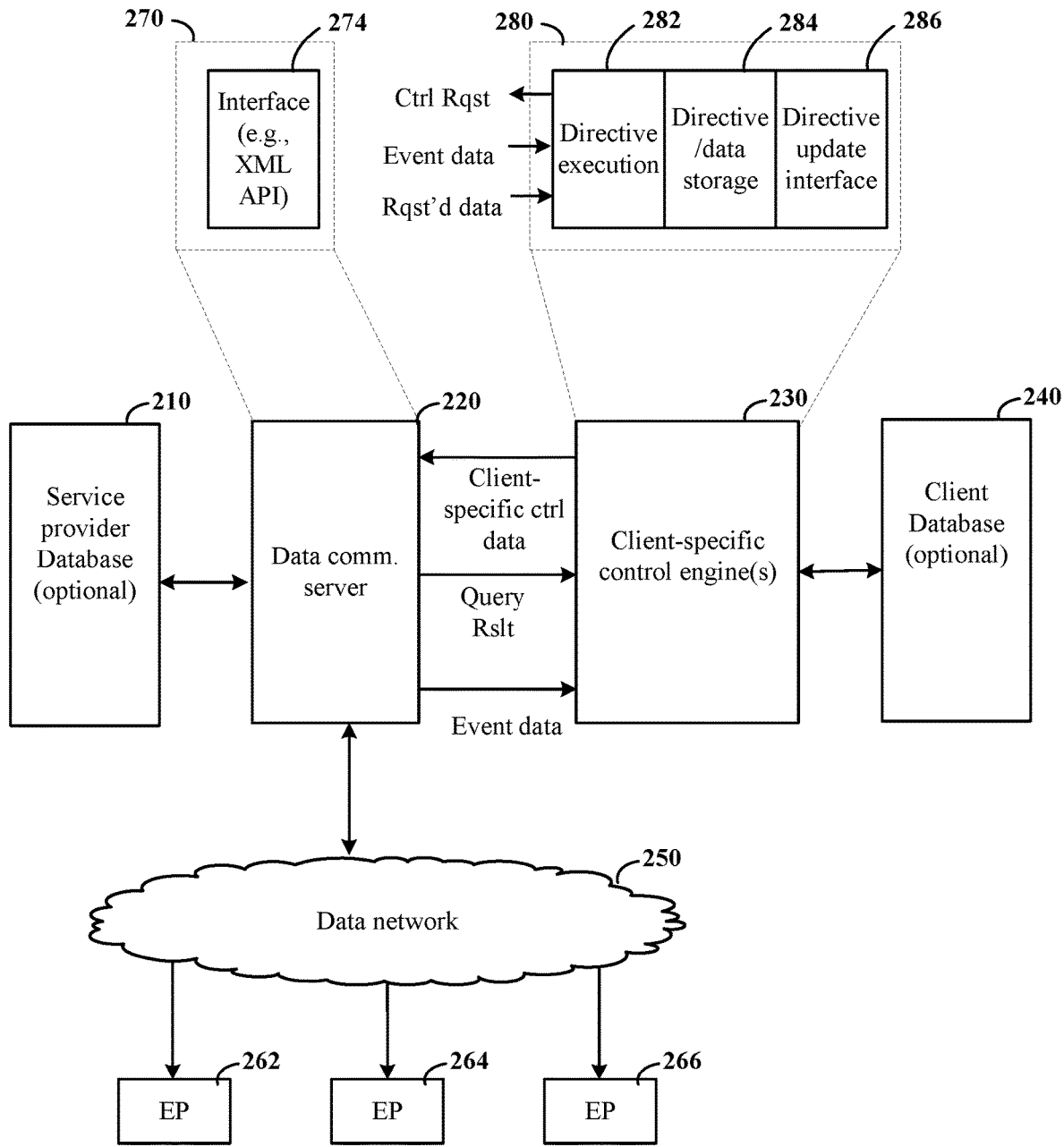
FIG. 2 is a block diagram of a communication control engine with high-level programmable language logic for two different languages, consistent with embodiments of the present disclosure.

FIG. 2 is a block diagram of a communication control engine with high-level programmable language logic for two different languages, consistent with embodiments of the present disclosure. The system includes a data communications provider server 220 configurable to provide one or more virtual office features for a plurality of endpoint devices 262, 264, and 266 connected in a data network 250. The endpoint devices may include VoIP-enabled devices (e.g., IP phones, smart phones, tables, and/or desktop computers) and/or non-VoIP endpoint devices (e.g., plain old telephone service (POTS) telephones and cellular-capable devices). Each endpoint device is respectively associated with an account of a respective client.

The system includes a processing circuit(s) configured to implement client-specific control engines 230. The client-specific control engines 230 are configured, as described with reference to client-specific control engines 120, to adjust the virtual office features (e.g., data communications) provided for each client account according to a respective set of control directives. For instance, the client-specific control engines 230 may dynamically adjust privacy policies associated with the virtual office features provided to a client entity, as defined in the one or more sets of control directives specified for the client entity.

As described with reference to FIG. 1, the control directives for a client account may generate client-specific sets of control data based on various data metrics including for example, data communication events or data received from the data communication server, data acquired from a client (e.g., from a client database), and/or data provided by third parties (e.g., third party monitoring services). In some embodiments, the control directives may cause the client-specific control engine 230 to query data from a client database 240 or from a service provider database 210. In some embodiments, the control directives may cause the client-specific control engine 230 to issue an analytics request specifying a particular evaluation of data in a database (e.g., 210 or 240). For example, client-specific control data communicated to the data communications provider server 220 may prompt the data communications provider server 220 to perform a particular analytical evaluation of data stored in the service provider database 210 (such as to determine the level of sensitivity of the requested data). After completing the requested evaluation, the data communications provider server 220 communicates the result back to the requesting client-specific control engine 230. Data retrieved from the databases and/or via analytics evaluation may be used, for example, to dynamically adjust the virtual office features provided during operation. Based on the evaluation of the sensitivity of the requested data, the data communications provider server 220 may implement different and/or additional privacy protection processes while providing the data communications via the data network 250.

The client-specific control engines 230 communicate the client-specific control data to the data communication server (s) using an interface protocol having an instruction format that is independent of an instruction format used to implement the client-specific control engines 230 and/or client-specific control directives. As previously described, the independent instruction format of the interface protocol allows clients to write programming instructions, for example, using their preferred high-level programming and/or may be used to limit customer access and/or control over the data communications provider server. For example, the interface protocol may be configured to allow the client-specific control engines to request analysis of data in the service provider database 210 without allowing direct access to the raw data stored therein. Similarly, the client-specific control engines may be configured to request analysis of data in the client database 240, without allowing direct access to the raw data stored therein.

As described with reference to FIG. 1, client-specific control engines 230 may be implemented in various locations. For example, client-specific control engines 230 for a particular client account may be implemented in the data communications provider server(s) 220, in a separate processing circuit communicatively connected to the data communications provider server(s) 220, using one or more processing circuits of the client, or a combination thereof.

The data communications provider server 220 and client-specific control engines 230 may be implemented using various circuit arrangements. Block 270 shows an example implementation of a data communications provider server configured to provide a data communications IPBX service for a client. The example data communications provider server 270 includes one or more IPBX server(s) configured to establish and direct data communications for a plurality of endpoints of a customer account. Interface circuit 274 is configured to allow different client specific control engines to communicate with the data communications provider server 220 via a common high-level language instruction set (e.g., a set of XML instructions).

Block 280 shows an example implementation of a client-specific control engine 230. In this example, the client-specific control engine includes a storage circuit 284 configured to store control directives and/or data for one or more client accounts. Directive execution circuit 282 is configured to provide client-specific control of the remote services provided for a client via execution of the control directives for the client stored in storage circuit 284. In some implementations, the directive execution circuit 282 is configured to communicate client-specific control data to the data communications provider server 220, for example, via an interface, using a high-level language instruction set (e.g., a set of extensible meta-data language (XML) instructions). Additionally or alternatively, the directive execution circuit 282 may retrieve one or more sets of directives from an external source (e.g., a client database). In this example, the client-specific control engine shown in block 280 includes a directive update interface circuit 286 configured to facilitate upload and/or editing of control directives for a client account.

Figure 3:
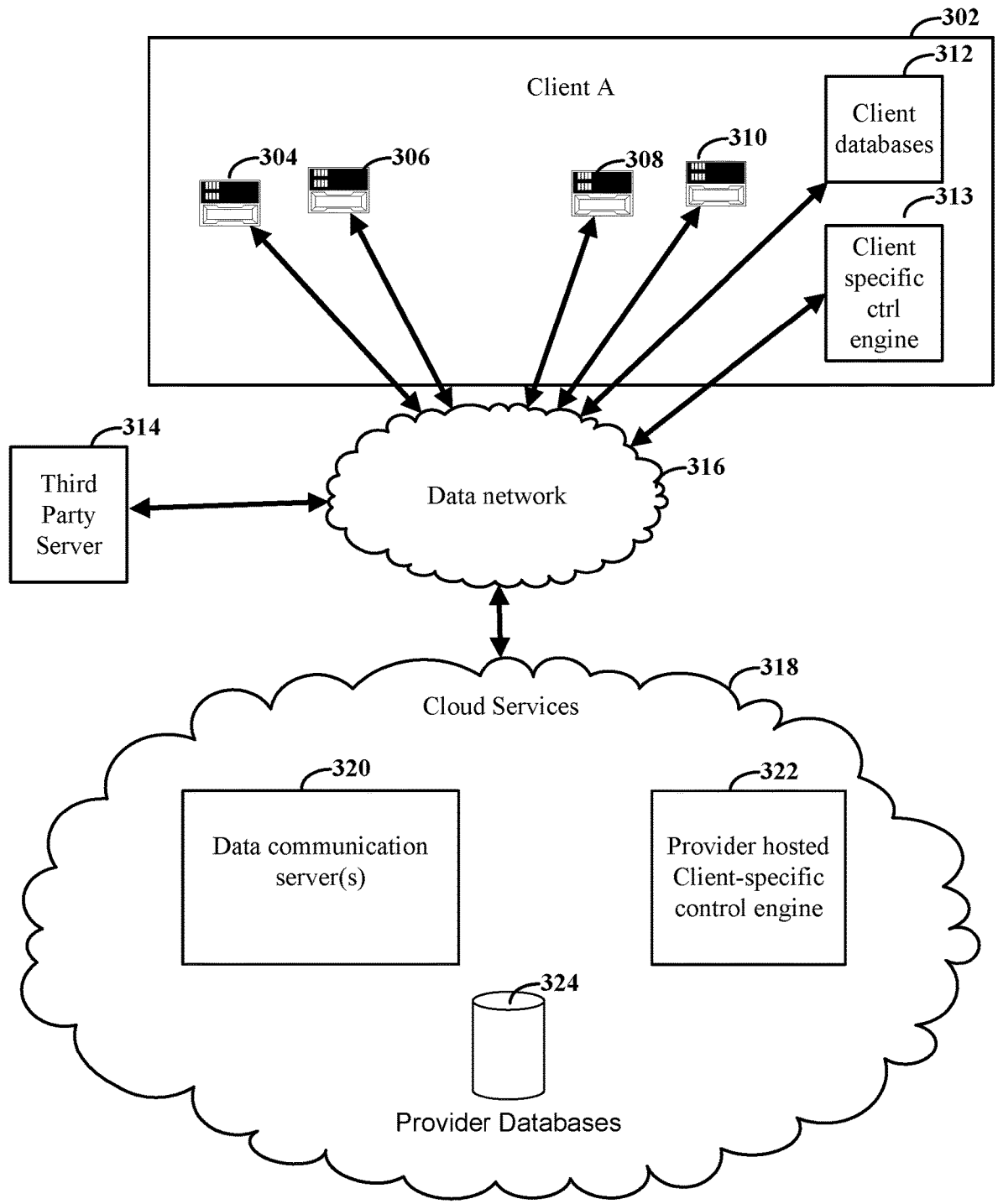
FIG. 3 is a diagram for communication privacy protection using a high-level programming language, consistent with embodiments of the present disclosure.

FIG. 3 is a diagram for communication privacy protection using a high-level programming language, consistent with embodiments of the present disclosure. In connection with these specifically-illustrated examples, data communications endpoint devices 304, 306, 308, and 310 connected in a data network 316 are configured to place and receive data communications between other data communications endpoint devices, and/or between non-data communications endpoint devices. Non-data communications endpoint devices may include, for example, plain old telephone service (POTS) telephones and cellular-capable devices, which might also be data communications capable (e.g., smart phones with appropriate data communications software applications). The various endpoint devices include circuitry that is specially configured to provide communications functions that include interfacing with the appropriate circuitry of the communication service provider used by the corresponding endpoint device. In many contexts, a data communications endpoint device is a data communications-capable telephone commonly referred to as IP phones. The data communications endpoint devices can include, but are not limited to, desktop computers, mobile (smart) phones, laptop computers, and tablets. When each of the endpoint devices originates or receives a communication in a telephone network, each can be characterized or referred to as an addressable communication endpoint.

The communication routing and other services for the data communications can be provided by one or more data communications servers 320 within a cloud services system 318 (e.g., configured to provide virtual office features to customers of the data communications provider). In particular example embodiments, the data communications servers 320 can be located within the cloud services system 318. The cloud services system 318 also includes one or more provider hosted client-specific control engines 322, configured as described with reference to 230 in FIGS. 2 and 120 in FIG. 1. A client-specific control engine 313 may also be implemented locally by a client (e.g., 302). In some embodiments, data centers can be part of a cloud services system 318 where the hardware providing the cloud services is located in a number of different data centers with different physical locations. Consistent with embodiments, the cloud services can include SIP servers, media servers, and servers providing other services to both data communications endpoint devices and the users of the data communications endpoint devices. In some instances, the various servers, including both the data communications servers and data analytic servers discussed herein, can have their functions spread across different physical and logical components. For instance, a cloud-based solution can implement virtual servers that can share common hardware and can be migrated between different underlying hardware. Moreover, separate servers or modules can be configured to work together so that they collectively function as a single unified server.

A particular example of a data communications server uses session initiation protocol (SIP) to handle various communication functions (e.g., communication setup and tear down); however, the various embodiments discussed herein are not necessarily limited thereto. Consistent with the above and other embodiments disclosed herein, the data communications servers can be configured to establish a portion of the communication from the data communications endpoint devices to another data communications endpoint device, or to a gateway.

According to various embodiments, one or more data analytics servers can monitor and analyze communication data relating to the data communications servers and data communications endpoint devices. For example, a data analytics server can be designed to track communication statistics about various different communication-related parameters, such as communication duration, communication date, communication time of day, contacted parties, endpoint devices, selected data centers, selected carriers, dropped communications, transferred communications, voicemail access, conferencing features, and others. The high-level programming language(s) and the data communications servers executing the languages can access the communication summary metrics and the data analytics, which can be stored in a provider database 324. For example, a script running the data communications server could parse communication processing XML (CPXML) documents to generate database queries that direct the data communications server to query, or subscribe to, communication length summaries for all communications made to endpoints that are registered to the data communications server. The script could then use the information to control how data communications are routed as well as how different (customer or provider) services are invoked. According to various embodiments, the database queries could be sent to a customer database 302.

Consistent with certain embodiments, the data communications server can be configured to interface with customer databases 312, or with third party servers 314. For instance, a CPXML document stored by the cloud services system 318 can identify, based upon a received communication, a Uniform Resource Identifier (URI) that points to customer databases 312, or to a third party server 314. Control directives provided from these servers, for example, in the form of a CPXML document can be used to specify communication routing, or other functions.

Figure 4:
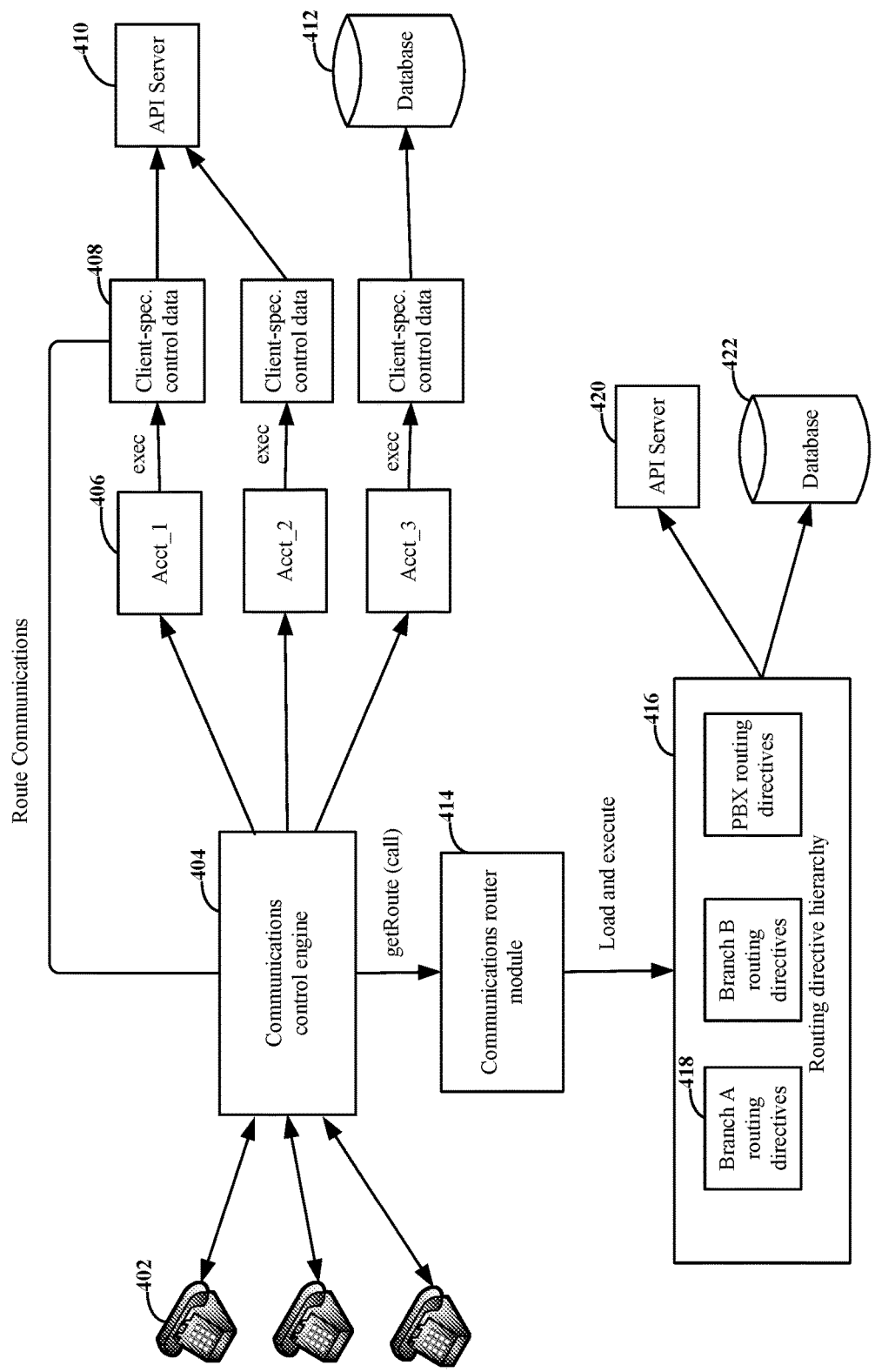
FIG. 4 is a block diagram showing the use of a hierarchy of programmable language documents, consistent with embodiments of the present disclosure.

FIG. 4 is a block diagram showing the use of a hierarchy of programmable language documents, consistent with embodiments of the present disclosure. Communication control engine 404 can provide communication flow control and routing in a manner that can be consistent with discussions found herein and relating to communication control engines, data communications servers, and the other figures. Consistent with various embodiments, the communication control engine 404 is a PBX that is part of a data communications system. For instance, the PBX can be configured using Java-based applications that manage voice over IP networks. The PBX can be hosted by a data communications service provider and located at one or more data centers. Various PBX features can be provided, such as communication forwarding, remote pickup, communication routing, and voice mail.

Consistent with various embodiments, customers of a data communications provider can use the data communications system by generating documents written in both CRXML and CPXML. Together, the documents specify how the customer would like communication intercept to be handled for both inbound and outbound communications. For instance, a CPXML document 408 can be associated with an extension account 406, or with groups of extension accounts. The extension accounts 406 can represent a specific individual and their associated extension number(s). A CPXML document 408 that is configured in this manner will be invoked by the communication control engine 404 after an incoming communication is routed to an extension that has CPXML capabilities enabled. CPXML documents can also be used for communication flow processing of outbound communications. The CPXML document may provide logic for sophisticated communication control functions for outbound communications. For example, messages (e.g. text messages and email messages) can be automatically generated in response to outgoing communications and restrictions can be placed on outbound communications based upon factors such as time of day or communication history.

The communication control engine 404 may also consult with communication routers 414. The communication routers can be programmed using CRXML documents 418, and with JavaScript for dynamic data access and logic handling. The CRXML documents 418 can be arranged in router xml hierarchy 416, which can specify different CRXML documents 418 depending upon the branch or PBX that is identified as corresponding to the communication. Once the communication router documents are loaded, they can be cached in memory and used by the communication control engine 404 to make a routing decision. When a communication is routed through the communication control engine 404, the communication control engine can consult with high-level CRXML documents. The branch level can be identified, for example, based on the branch Id of caller (for outbound calls) or callee (for inbound calls). Delineations other than the branch are also possible, such as by the called country, the particular store, the state, or other. If a route result is not determined, the communication control engine 404 can also consult with PBX-level CRXML document to obtain routing decisions. Examples of a route result from a script are "Accept," "Reject," or "NewRoute." Thus, the programmable communication router (CRXML) module 414 provides the communication control engine 404 with the ability to handle communication intercept/filter reject or re-route the communication to a different target destination.

The communication router module 414 can also interact with a CPXML document to handle sophisticated communication flow scenarios where the communication routing is changed after the initial determination. For example, the CPXML can include commands (e.g., "reroute") that the communication control engine 404 uses to provide feedback to the programmable communication routers 414, which use CRXML for initial routing decisions. This might allow, as an example, a CRXML routing decision to be overridden by the CPXML document(s).

According to particular embodiments, the programmable communication routers (using CRXML) 414 can be viewed as plugins to the communication control engine 404. The communication router plugins may have two levels—Branch and PBX levels. The communication router supports CRXML-defined structures that specify how the PaaS can be utilized by a customer. For example, the CRMXL can define sets of conditional statements, data access requests, and communication routing commands: if/else, condition, goto, log, var, script, query, data, accept, reject, route statements, or other similar commands. In particular embodiments, CRMXL can be considered a subset of CPXML by containing a part, but not all, of the CPXML communication flow commands. This distinction can be useful for keeping CRMXL documents light weight so that communication routing decisions are simplified and efficient. More complex tasks, such as the use of media and advanced communication handling, can be handled using CPXML. Using such programmable communication routes, a few example uses include: school district that generates SMS/Email notifications to parents whenever an emergency number is dialed; off hour restriction of outbound communication with CPXML; communication center lockdown to provide outbound dialing restriction for phones; computer initiated dialing with caller identification (ID) override based destination database table, and communication return to target DID/agents; and implementation of a communication black list (denying communications to/from the list) or white list (allowing communications to/from the list) with potentially large lists and dynamic updating capabilities.

Consistent with embodiments of the present disclosure, both CRXML and CPXML provide the capability of handling dynamic data from multiple sources. Examples of these sources are depicted as application program interface servers 410, 420 and databases 412, 422. The dynamic data can therefore be provided from a variety of sources including, but not necessarily limited to, communication route session data (caller id, callee id, or route from/to), query custom object (to a database) in the data communications provider system/cloud, and access data through HTTP RESTful API. For instance, the XML documents can include a web resource that is identified by Uniform Resource Identifiers. The web resource might be a customer HTTP server that responds to a conditional query (e.g., whether or not a communication queue is above a threshold) with CPXML code that instructs the communication control engine on how to route, or otherwise handle, the communication. In such a manner, client-specific sets of control data provided by the communication control engine may allow for adjusted (e.g., customized) virtual office features for end users (such as 402) of the data communications system.

Figure 5:
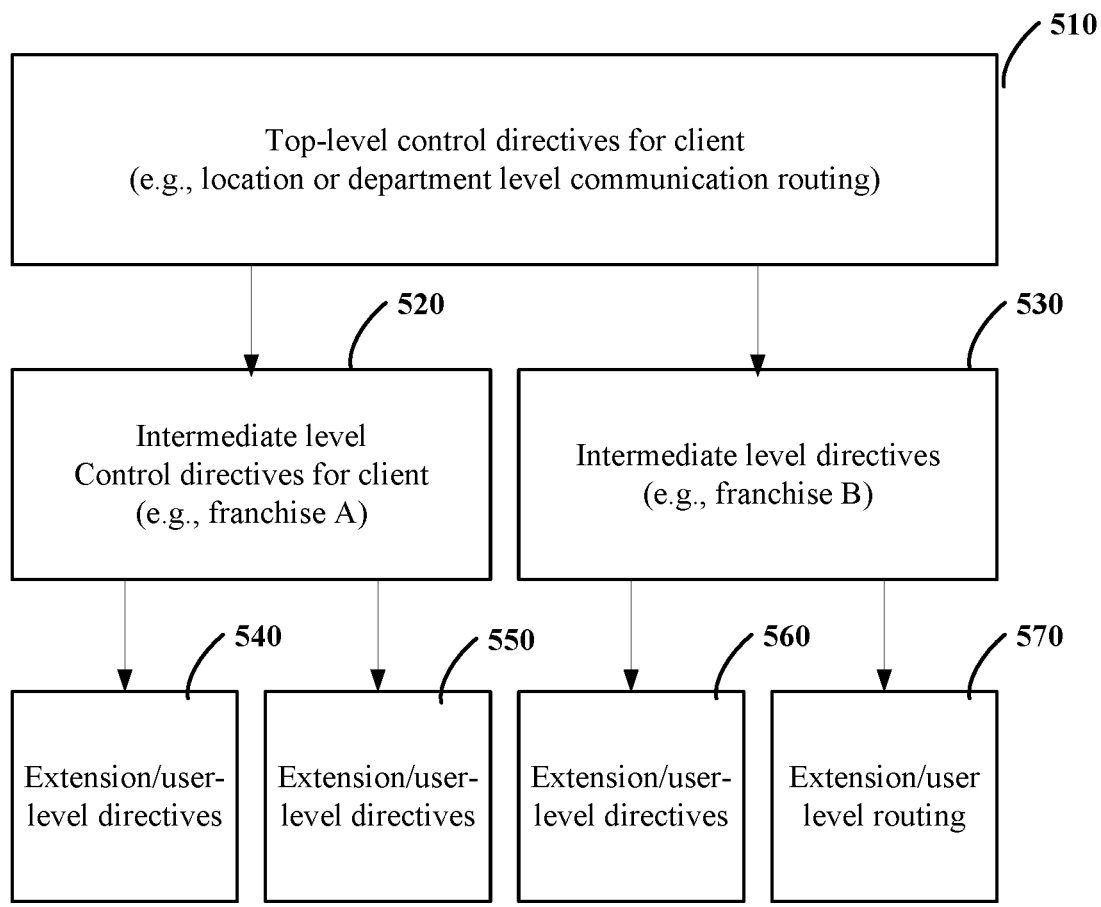
FIG. 5 is a block diagram showing an example set of control directives configured for multiple levels of control, consistent with embodiments of the present disclosure.

FIG. 5 is a block diagram showing an example set of control directives configured for multiple levels of control, consistent with embodiments of the present disclosure. The control directives described herein can be used to form programming instructions which can be transmitted to the data communications provider for adjusting the virtual office features provided to the client entity. In this example, block 510 provides a set of top-level control directives that are applicable to all data communications for a client. Blocks 520 and 530 show a set of intermediate-level control directives that are applicable only to a subset of endpoints included in the client account (e.g., for respective IPBXs, branches, department, and/or franchisees). Blocks 540, 550, 560, 570 are shown as lower-level control directives that are applicable to particular extensions and/or end-users of the client account. The lower-level control directives may be useful, for example, for an end-user to customize and/or dynamically adjust direction of communications to an extension throughout the day.

Figure 6:
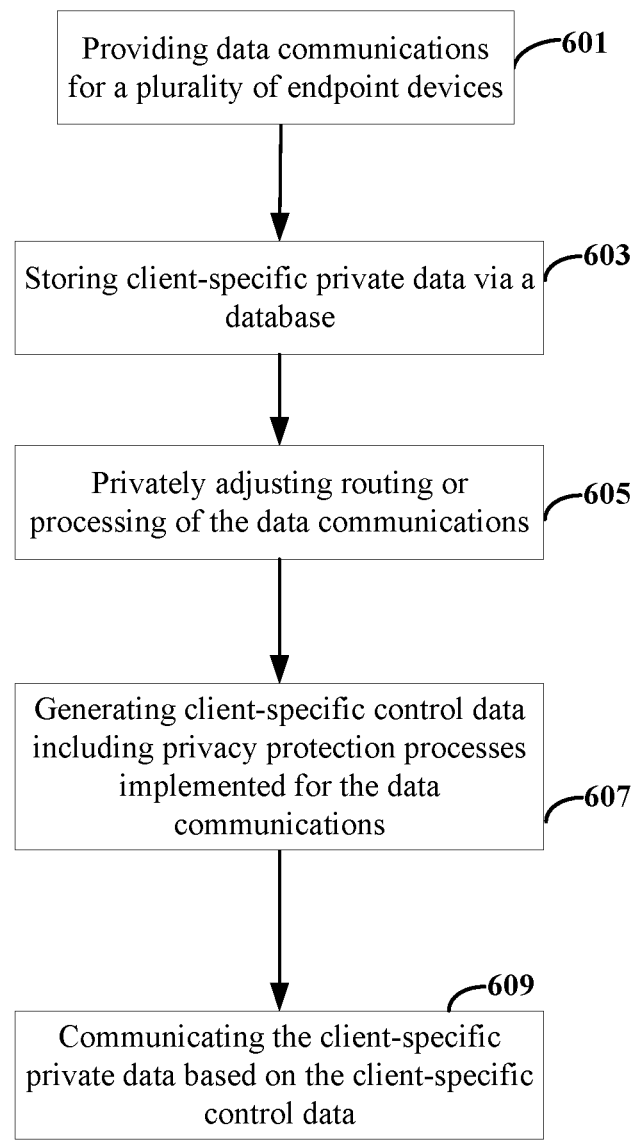
FIG. 6 is a flow diagram showing a method of communication privacy protection using a high-level programming interface, consistent with embodiments of the present disclosure.

FIG. 6 is a flow diagram showing a method of communication privacy protection using a high-level programming interface, consistent with embodiments of the present disclosure. At 601, the method includes providing data communications for a plurality of endpoint devices. As discussed herein, each of the plurality of endpoint devices is respectively associated with an account of a respective one of a plurality of remotely-situated client entities. The data communications can be provided to the plurality of endpoint devices using a first programming language that relates to a message exchange protocol between a data communications provider and data sources by routing the data communications for the endpoint of each of the client entities. At 603, the method includes storing client-specific private data, via a database. Specific, non-limiting examples of such client-specific private data include patient records, financial records, and/or social security information, among others.

At 605, the method includes privately adjusting routing or processing of the data communications for one of the remotely-situated client entities, via a processing circuit communicatively coupled to the database. The routing or processing of the data communications can be privately adjusted by generating client-specific control data including privacy protection processes implemented for the data communications, at 607. For instance, for one remotely-situated client entity, client-specific control data can be generated based on programming instructions received from the one remotely-situated client entity over the message exchange protocol, the programming instructions corresponding to a second programming language that is compatible with the first programming language and including privacy protection processes implemented for data communications including the one remotely-situated client entity.

At 609, the method includes communicating the client-specific private data based on the client-specific control data. For instance, in response to receipt of data communications involving the one remotely-situated client entity, the method includes communicating the client-specific private data based on the client-specific control data. As an illustration, the method can include transmitting the data communications in accordance with medical record privacy requirements and/or making routing decisions based on private customer data. As another illustration, the method can include facilitating communication between a medical practitioner and a patient and selecting the medical practitioner to communicate with the patient based on private customer data. Incoming communications can be routed from the patient to the selected medical practitioner, using the high-level programming language and in accordance with the client-specific control data. Yet further, incoming communications can be routed to admitted patients using private patient data and based on the client-specific control data. In some example embodiment, the client entity includes a plurality of locations and each location maintains private data that is inaccessible to the other locations. In such example embodiments, the method includes routing communications to the appropriate location without exposing private data associated with the other locations based on the client-specific control data.

More Detailed and/or Experimental Embodiments

Consistent with the above-characterized embodiments, various other embodiments are based on implementations which involve alternative features and/or involving a type of programming language which is different than disclosed above for use as part of the above embodiments. Accordingly, the present disclosure is not necessarily limited to specific methods, systems, applications and devices in and stemming from the specific embodiments disclosed herein. Other related embodiments and aspects can be fully incorporated in each such disclosed (contemplated/suggested) embodiment. Some of these aspects and embodiments would be recognized from the following discussion.

In certain embodiments, the client-specific control engines provide client-specific control data to the data communications server(s) via an interface protocol platform that characterizes the format in which the client-specific sets of data are communicated to the data communications server. According to various embodiments, data is communicated via the interface protocol platform using high-level programming language instruction set. The high-level programming language instruction set allows a programmer access to the data communications server(s) (or PaaS computing server(s) providing remote services) by way a controlled and limited set of communication control operations and functions. The limitations on the operations can be particularly useful for allowing programming control to be placed into the hands of different customers of the provider of the data communications servers. For example, the provider can update or make other changes to how the data communications servers are configured without requiring modification to documents written to use the high-level language, which might otherwise be required to account for the changes. Moreover, the data communications servers and their data can be protected from poor programming decisions (intentional or otherwise) by tightly controlling the extent that the documents provide control or access the inner workings of the data communications servers.

Consistent with the above discussion, at the client side of the data communications services, the client's computer-based processing (e.g., by the client-specific control engine) generates and submits control (routing/data-communication) directives for assessment and use by the data communications service provider. In a typical implementation, these directives can be realized using codes or one or more commands (or a script of program-created commands). As examples, such codes or command sets can be implemented using a variety of programming control approaches. These approaches include, for example, a programming language (such as C++, WL, JAVA, HTLM, SQL, etc.) common to both the client-specific control engine and to the data communications service provider, which receives the directives (submitted from the client side) for adjusting the data communications services being provided to the submitting client. In some implementations, look-up tables with codes/commands as entries can be used by the client engines each time a service change is needed. The entries can be pre-generated by the service provider for use by the client, manually entered by either the client or an installer, and/or generated by logic circuitry (such as implemented in hosted FPGA fabric). For instance, entries may be generated by logic circuitry based on a set of limited assumptions and conditions applicable to that specific type of client and its service expectations/subscription (e.g., no more than 10 extension phone lines in any designated geographic region, only 2 designated extension lines permitted to videoconference, etc.).

By using a common interface protocol (e.g., the programming language, codes or command sets) which is understood by the data communications service provider, authentication and updating for added (telephony) services is readily achieved automatically and remotely without burdening the data communications service provider with cost-intensive set up procedures. Depending on the level of services being added/changed for each client, and/or depending on the client's manual-operator and/or automated technology, the control directives can be generated and submitted in various (coded) ways such as described above and also, for example, by dial tone input generated remotely on behalf of each client, by smartphone app specific to the client, by voice recognition, or combinations thereof. The client engine can also prompt the user to effect and select decisions upon certain client-generated or provider-prompted events. Consistent with the instant disclosure, control directives can be generated by the client (and/or client engines) based on various criteria/parameters According to embodiments of the present disclosure, the data communications servers can be configured to use different high-level programming languages for different functions, where each programming language has a different set of commands. For example, a first high-level programming language can be used to create documents that control communication routing decisions for high volumes of communication traffic, as might occur at the edge of a data communications provider's system. These communication routing decisions can, for example, identify a particular branch office or an IPBX of a particular customer. The identified IPBX might then have additional documents written to communicate using a second high-level programming language that is tailored toward more specific communication processing capabilities that might be associated with a particular account or another identifiable grouping. The distinction between the two programming languages can be particularly useful in terms of improving the scalability of the system. For instance, the language used for communication routing decisions can be relatively light weight, with fewer commands and capabilities. In particular implementations, the first (communication routing) language can contain a subset of the commands available in the second (communication processing) language.

According to various embodiments, the high-level, domain-specific programming language(s) are defined using a markup language as the basis for the language structure. More particular embodiments use extensible markup language (XML). An XML model defines the constraints on the high-level language, including defining the set of valid commands that can be carried out by the data communications servers. Within these constraints, a customer can write XML code that self-describes the building blocks used in the customer's particular application. Another aspect of the communication processing XML is that it allows for various different data structures to be embedded into the XML document or file. For example, a script written in JavaScript can be embedded as character data that the data communications servers are configured to identify and execute. Unless otherwise stated, the use of XML in connection with various embodiments does not necessarily limit the corresponding embodiments, such as limiting the embodiments to the use of only an XML-based language(s).

Particular implementations relate to the use of two separate languages, one that can be used for initial communication routing and the other for providing more complex and specific communication processing functions. In various portions of the present disclosure, the two languages are referred to as either communication processing XML (CPXML) or communication routing XML (CRXML).

The data communications servers providing the underlying function for the PaaS can be configured to utilize a high-level, domain-specific programming language. A particular example language is referred to as Communication Processing eXtensible Markup Language (CPXML). CPXML refers to a communication processing language which defines the message exchange protocol between a communication control server (e.g., an IntraSwitch with a CPXML Engine) and other sources of information, such as databases, web applications, authentication servers, and servers providing various communication-related services. CPXML can allow developers to program communication processing logic or service execution logic with both XML building blocks and JavaScript/TCL, or other scripting languages. In certain implementations, CPXML allows PaaS customer developers to program and integrate data communication flow (e.g., as provided by a cloud-based data communications service) with customer or third party application servers and databases.

A CPXML engine can send requests to a web server and get XML (CPXML) responses for processing, thereby operating in a stateless manner that is similar to HTML/Internet browser. The CPXML engine can interpret a received CPXML response, and render (execute) CPXML building blocks. Each building block can define functions relating to voice, communication control, and flow control logic. The CPXML engine may also execute other types of code, such as JavaScript, to create dynamic content (e.g., dynamically generated CPXML) for client-side flow control. Each CPXML document may have URL links to a web server for iterative processing, or it may include query requests for retrieving data from various sources. A query could be formatted for consistency with the source of the data (e.g., by using JavaScript Object Notation (JSON) to retrieve data from third party application servers or from the data communications server provider's cloud database). This information can then be used to drive communication flow or communication control decisions.

CRXML defines a limited set of commands to the communication routing logic that allows a customer to define how a communication is initially routed. Maintaining the CRXML as a limited set of simple building block commands can help with the efficiency of the communication control switch. For example, the communication control switch can be located at the perimeter of the data communications provider's routing network, which implies that it may be required to handle a large volume of data communications telephone communications. The efficiency in processing the large volume of communications can have a significant impact on the performance of the system.

Consistent with various embodiments, the CRXML documents specify a first level of communication routing and simple communication processing that are carried out by the communication control switch. For example, a communication control switch may provide communication routing options for multiple branch offices or locations and for multiple PBXs that support the branch locations. Each branch and PBX may have multiple customer (user) accounts associated therewith. CRXML documents can be used to determine the routing for a communication by identifying a particular branch location, a particular PBX and particular data communications customer account to use in subsequent communication processing and routing. The initial routing decision is indicated by the arrow labelled as "account selection," which shows the passage of control to a communication processing engine.

Various blocks, modules or other circuits may be implemented to carry out one or more of the operations and activities described herein and/or shown in the figures. As examples, the Specification describes and/or illustrates aspects useful for implementing the claimed invention by way of various circuits or circuitry using terms such as blocks, modules, device, system, unit, controller, and the like. In these contexts, a "block" (also sometimes "logic circuitry" or "module") is a circuit that carries out one or more of these or related operations/activities (e.g., a communication control circuit). For example, in certain ones of the above-discussed embodiments, one or more modules are discrete logic circuits, computer processing circuits, or programmable logic circuits configured and arranged for implementing these operations/activities, as in the blocks shown in the figures.

Similarly, it will be apparent that a server (e.g., providing a corresponding software platform) includes a computer processing circuit that is configured to provide services to other circuit-based devices. Moreover, a (data communications) endpoint device (or endpoint) includes a communication circuit and (computer) processing circuits which are configured to establish (data communications) communication sessions with other endpoint devices (e.g., personal computers, IP-enabled mobile phones, and tablet computers). In certain embodiments, such a processing circuit is one or more computer processing circuits programmed to execute a set (or sets) of instructions (and/or configuration data). The instructions (and/or configuration data) can be in the form of software stored in and accessible from a memory circuit, and where such circuits are directly associated with one or more algorithms (or processes), the activities pertaining to such algorithms are not necessarily limited to the specific flows such as shown in the flow charts illustrated in the figures (e.g., where a circuit is programmed to perform the related steps, functions, operations, activities, etc., the flow charts are merely specific detailed examples). The skilled artisan would also appreciate that different (e.g., first and second) modules can include a combination of a central processing unit (CPU) hardware-based circuitry and a set of computer-executable instructions, in which the first module includes a first CPU hardware circuit with one set of instructions and the second module includes a second CPU hardware circuit with another set of instructions.

Certain embodiments are directed to a computer program product (e.g., nonvolatile memory device), which includes a machine or computer-readable medium having stored thereon, instructions which may be executed by a computer (or other electronic device) that includes a computer processor circuit to perform these operations/activities. For example, these instructions reflect activities or data flows as may be exemplified in figures, flow charts, and the detailed description.

Based upon the above discussion and illustrations, those skilled in the art will readily recognize that various modifications and changes may be made to the various embodiments without strictly following the exemplary embodiments and applications illustrated and described herein. For example, although aspects and features may in some cases be described in individual figures, it will be appreciated that features from one figure can be combined with features of another figure even though the combination is not explicitly shown or explicitly described as a combination. Such modifications do not depart from the true spirit and scope of various aspects of the disclosure, including aspects set forth in the claims.

What is claimed is:

1. An apparatus for privacy protection in a communication system, the apparatus comprising:
    a communication server configured to:
        interface with remotely-situated client entities using a first programming language that relates to a message exchange protocol between a data communications provider and data sources; and
        provide data communications for a plurality of endpoint devices, each respectively associated with an account of a respective one of a plurality of disparate client entities, by routing the data communications for the endpoint of each of the client entities;
    a database storing client-specific private data; and
    a processing circuit communicatively coupled to the database and to the communication server, the processing circuit being configured and arranged to:
        privately adjust routing or processing of the data communications for one of the disparate client entities by:
            generating, for the one disparate client entity, client-specific control data based on programming instructions received from the one disparate client entity over the message exchange protocol, the programming instructions corresponding to a second programming language that is compatible with the first programming language and including privacy protection processes implemented for data communications including the one disparate client entity; and
            in response to receipt of data communications involving the one disparate client entity, communicating the client-specific private data based on the client-specific control data.

2. The apparatus of claim 1, wherein the data communications are transmitted in accordance with medical record privacy requirements.

3. The apparatus of claim 1, wherein a processing engine makes routing decisions based on private customer data.

4. The apparatus of claim 1, wherein the system facilitates communication between a medical practitioner and a patient.

5. The apparatus of claim 4, wherein the medical practitioner is selected to communicate with the patient based on private customer data.

6. The apparatus of claim 4, wherein medical records of the patient are forwarded to the medical practitioner using high-level programming language.

7. The apparatus of claim 4, wherein the processing circuit is configured to route incoming communications from the patient to a selected medical practitioner.

8. The apparatus of claim 1, wherein the processing circuit is configured and arranged to route incoming communications to admitted patients using private patient data.

9. The apparatus of claim 1, wherein the client entity includes a plurality of locations and each location maintains private data that is inaccessible to the other locations, the processing circuit being configured and arranged to route communications to the appropriate location without exposing private data associated with the other locations.

10. An apparatus for privacy protection in a communication system, the apparatus comprising:
    a database storing a set of client-specific private data; and
    a computing server configured and arranged to:
        provide data communications for a plurality of extensions, each respectively associated with an account of a respective client entity; and
        interface with a data communications server configured and arranged to provide virtual office features to the extensions based on a subscription; and
    a processing circuit communicatively coupled to the computing server and the database, the processing circuit configured and arranged to:
        receive from the data communications server, a set of instructions written in a first programming language that relates to a message exchange protocol between the data communications server and data sources;
        generate programming instructions corresponding to a second programming language that is compatible with the first programming language and including privacy protection processes implemented for data communications including the respective client entity; and
        facilitate private routing or processing of the client-specific private data by the data communications server by communicating the programming instructions including the privacy protection processes to the data communications server.

11. An method for privacy protection in a communication system, the method including:
    providing data communications for a plurality of endpoint devices, each respectively associated with an account of a respective one of a plurality of remotely-situated client entities using a first programming language that relates to a message exchange protocol between a data communications provider and data sources by routing the data communications for the endpoint of each of the client entities;
    storing client-specific private data, via a database; and
    privately adjusting routing or processing of the data communications for one of the remotely-situated client entities, via a processing circuit communicatively coupled to the database, by:
        generating, for the one remotely-situated client entity, client-specific control data based on programming instructions received from the one remotely-situated client entity over the message exchange protocol, the programming instructions corresponding to a second programming language that is compatible with the first programming language and including privacy protection processes implemented for data communications including the one remotely-situated client entity; and in response to receipt of data communications involving the one remotely-situated client entity, communicating the client-specific private data based on the client-specific control data.

12. The method of claim 11, including transmitting the data communications in accordance with medical record privacy requirements and based on the client-specific control data.

13. The method of claim 11, including making routing decisions based on private customer data and the client-specific control data.

14. The method of claim 11, including facilitating communication between a medical practitioner and a patient based on the client-specific control data.

15. The method of claim 14, including selecting the medical practitioner to communicate with the patient based on private customer data.

16. The method of claim 15, including routing incoming communications from the patient to the selected medical practitioner based on the client-specific control data.

17. The method of claim 14, including forwarding medical records of the patient to the medical practitioner using a high-level programming language and based on the client-specific control data.

18. The method of claim 14, including routing incoming communications to admitted patients using private patient data and based on the client-specific control data.

19. The method of claim 14, wherein the client entity includes a plurality of locations and each location maintains private data that is inaccessible to the other locations, the method including routing communications to the appropriate location without exposing private data associated with the other locations based on the client-specific control data.

* * * * *